United States Patent [19]
Raynes et al.

[11] Patent Number: 5,460,183
[45] Date of Patent: Oct. 24, 1995

[54] SWITCHABLE FILTER FOR REZEROING AN IN VIVO PRESSURE SENSOR

[75] Inventors: John W. Raynes, Sandy, Utah; Gary Altman, Kirkland, Wash.

[73] Assignee: Becton Dickinson and Company, Franklin Lakes, N.J.

[21] Appl. No.: 127,849

[22] Filed: Sep. 28, 1993

[51] Int. Cl.⁶ .......................................... A61B 5/00
[52] U.S. Cl. ............. 128/673; 128/675; 128/748; 73/4 R
[58] Field of Search ...................... 455/266, 307, 455/286, 193 B; 333/173, 175, 178, 101, 106, 107; 128/673, 675, 748, 672, 677, 668, 680–683; 364/572, 574; 73/4 R

[56] References Cited

U.S. PATENT DOCUMENTS

| | | | |
|---|---|---|---|
| 3,671,889 | 6/1972 | Favors | 33/175 |
| 4,151,474 | 4/1979 | Woollvin et al. | 333/173 |
| 4,244,262 | 1/1981 | Imai | 333/165 |
| 4,796,184 | 1/1989 | Bahr et al. | 128/682 |
| 5,191,327 | 3/1993 | Talmadge et al. | 364/572 |
| 5,243,990 | 9/1993 | Aung et al. | 128/681 |
| 5,280,790 | 1/1994 | Brooks | 128/681 |

Primary Examiner—Lee S. Cohen
Assistant Examiner—Robert L. Nasser, Jr.
Attorney, Agent, or Firm—Michael G. Schwartz; Eric M. Lee

[57] ABSTRACT

A filter for rezeroing an in-vivo pressure sensor is disclosed. The filter operates in a signal mode and a rezero mode. In the signal mode, the filter is a low pass filter which filters out noise. In the rezero mode, the filter is a low pass filter which filters out the dynamic components of an in-vivo pressure signal caused by the rezeroing of the pressure sensor. The filter is switchable between the signal and rezero modes. The filter is implemented by means of an active two pole RC filter with a Butterworth response. A circuit is provided to shorten the time in which the filter reaches its final response characteristic. Also disclosed is a method for processing an output from an in vivo pressure transducer, the output signal comprising noise, a mean pressure signal and a dynamic pressure signal. The method comprises the steps of: receiving as an input, the output signal from the pressure transducer; filtering out the noise from the received input by means of a first filter circuit; and, filtering out the dynamic pressure signal while passing the mean pressure signal by connecting a second circuit to the first filter circuit.

17 Claims, 2 Drawing Sheets

SWITCHABLE FILTER FOR REZEROING AN IN VIVO PRESSURE SENSOR

BACKGROUND

In the course of medical treatment, it is often desirable to measure the blood pressure of a patient. In the past this has been done by means of external pressure transducers. More recently, blood pressure has been measured by the placement of a pressure transducer directly inside a blood vessel of the patient or inside a catheter which is placed inside the patient's blood vessel. The placement of the transducer inside a blood vessel enables the observation of blood pressure waveforms having high dynamic fidelity.

All known blood pressure transducers experience some drift in their outputs at zero pressure. They must therefore be rezeroed to atmospheric pressure periodically. Rezeroing is typically accomplished by a control on the monitor to which the transducer is connected which adjusts the measured output signal to correct for the offset observed at zero (atmospheric) pressure.

Rezeroing a transducer placed inside the blood vessel presents unique difficulties, since the temporary removal of the transducer from the blood vessel to vent the tip of the atmosphere is a difficult procedure which presents risks to the patient when conventional rezeroing methods are used.

An in-vivo pressure transducer typically comprises a Wheatstone bridge mounted at least partially on a diaphragm. Rezeroing involves the equalization of the pressure on the bottom side of the diaphragm with that on the top side of the diaphragm. A method and apparatus for rezeroing a pressure transducer in-vivo are described in U.S. Pat. No. 5,203,340, which is incorporated by reference. Using the method and apparatus described and claimed in U.S. Pat. No. 5,203,340, the transducer can be rezeroed without removing the transducer from the blood vessel.

The in-vivo rezeroing of a pressure transducer has a peculiar limitation. The blood pressure typically seen by a pressure transducer in-vivo is dynamic and pulsatile. It takes a certain length of time for a pressure pulse wave to travel from the tip of the catheter, in which the transducer resides and at which the pressure wave impinges upon one side of the pressure transducer diaphragm, along the lumen of the catheter, through the rezeroing device and back to the other side of the pressure transducer diaphragm to accomplish the rezeroing. Thus, while the mean pressure on the diaphragm may be zero, a pulse artifact remains causing fluctuations of pressure about the mean.

Typical pressure monitors are adapted to detect pressure based on hydraulic coupling between the transducer and blood vessel. In such cases rezeroing is accomplished by means of an external stop-cock which can be used to establish an atmospheric datum pressure without producing any pulsations. Some monitors reject pressure pulses as being uncharacteristic of pressure transducers which are in the process of being rezeroed. Other monitors do not reject pulses but average the signals. They may not average the signals over a sufficiently long period of time to prevent integration errors. Either of these monitor characteristics will seriously limit the use of in-vivo pressure transducers using the method of rezeroing described above. There is therefore a need for a means by which an in-vivo transducer can be adapted for simple and effective rezeroing when used with typical pressure monitors.

SUMMARY OF THE INVENTION

The present invention is an apparatus for processing an output from an in vivo pressure transducer. The output signal is made up of noise, a mean pressure signal and a dynamic pressure signal. The apparatus is made up of the following: an input for receiving the output signal from the pressure transducer and a first filter circuit for filtering out the noise. The first filter circuit is connected to the input of the apparatus. A second circuit is provided for filtering out the dynamic pressure signal while passing the mean pressure signal. The second circuit is connected to the first filter circuit. The first filter circuit has an output for connecting the apparatus to a monitor.

A switch is provided for selectively electrically connecting the first filter circuit to the second filter circuit. The first and second filter circuits have low pass characteristics. In a second, less preferred embodiment, the first filter circuit is omitted.

The invention also includes a method for processing an output from an in vivo pressure transducer, the output signal comprising noise, a mean pressure signal and a dynamic pressure signal. The method comprises the steps of: receiving as an input, the output signal from the pressure transducer; filtering out the noise from the received input by means of a first filter circuit; and, filtering out the dynamic pressure signal while passing the mean pressure signal by connecting a second circuit to the first filter circuit.

DETAILED DESCRIPTION

Figure 1:
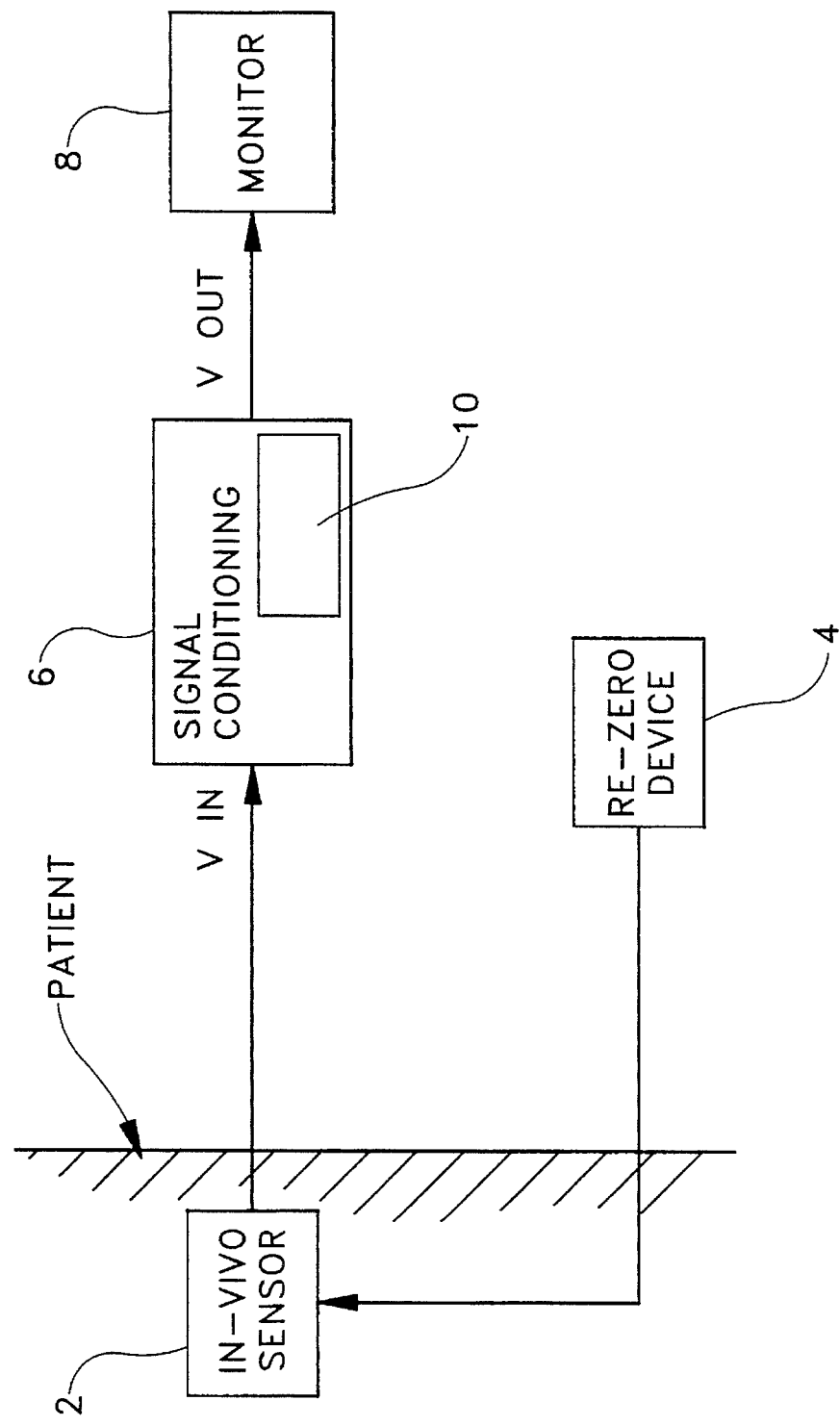
FIG. 1 is a block diagram of a typical blood pressure monitoring configuration utilizing the invention.
Figure 2:
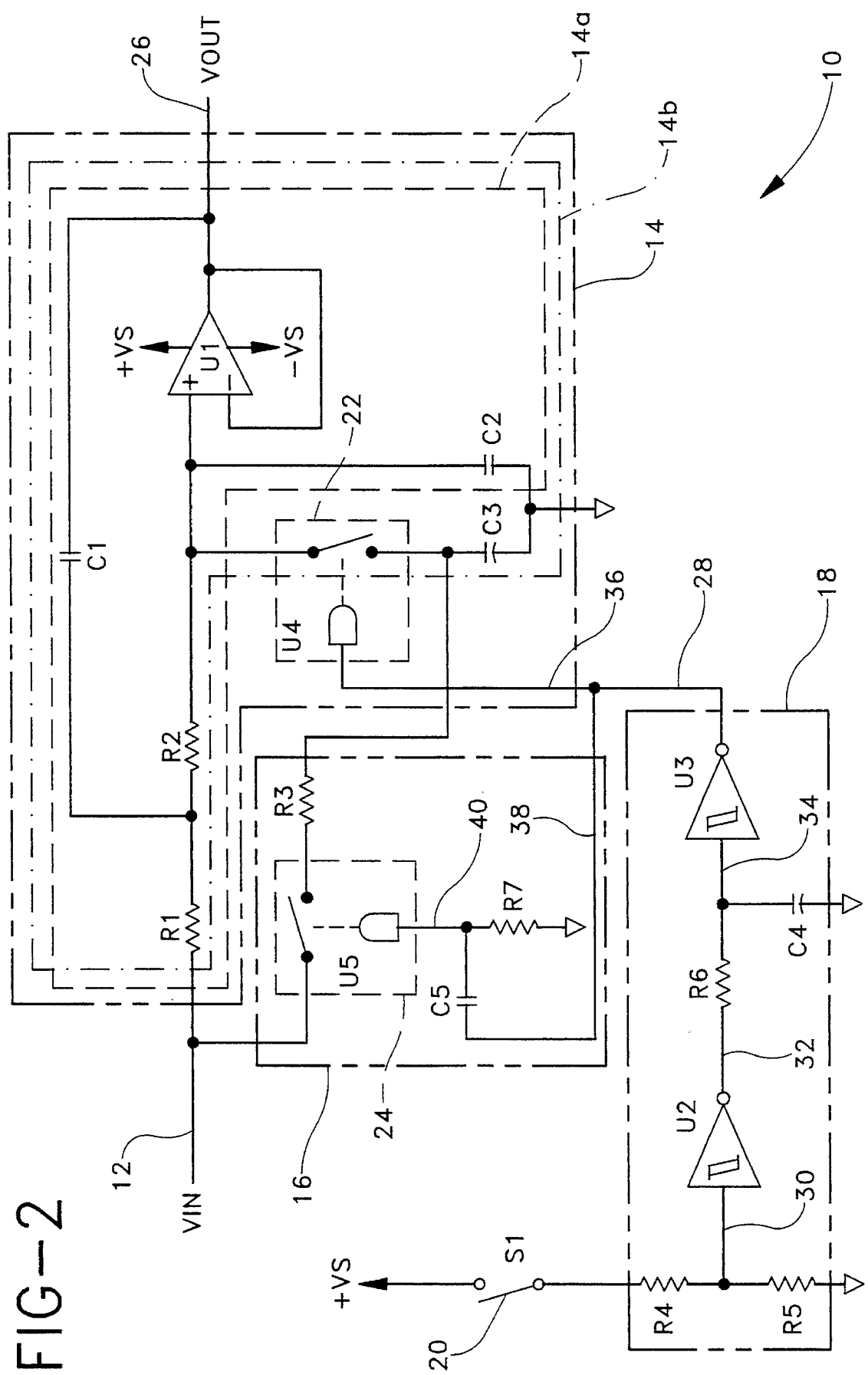
FIG. 2 is a schematic diagram of the invention.

Circuit 10 is part of signal conditioning circuit 6 linked to in-vivo sensor 2 and monitor 8. Pressure sensor 2 is capable of being rezeroed by ex-vivo rezero device 4.

Circuit 10 has input 12 which receives output signal $V_{in}$ from the in vivo pressure transducer (not shown). $V_{in}$ is made up of noise, a mean pressure signal and a dynamic pulsatile signal. Circuit 10 has an output 26 for connection to a standard blood pressure monitor. Circuit 10 can be divided into three main circuits, 14, 16 and 18. Switch 20 activates circuits 14 and 16 through debounce circuit 18.

Circuit 10 operates in two modes: signal mode and rezero mode.

Circuit 14 can be regarded as two circuits. The first circuit is a low pass filter made up of resistors $R_1$ and $R_2$, capacitors $C_1$ and $C_2$ and amplifier $U_1$. The second circuit is a low pass filter made up of resistors $R_1$ and $R_2$, capacitors $C_1$, $C_2$ and $C_3$ and amplifier $U_1$. The first and second circuits are thus electrically connected to each other. Circuit 14 is a switched low pass filter which has a first corner frequency in the signal mode and a second corner frequency in the rezero mode. The first corner frequency is chosen to filter out noise and artifact while preserving the frequencies necessary to monitor blood pressure. The second corner frequency is chosen to filter out the dynamic pulsatile signal. Third circuit 16 is a switching circuit, the purpose of which will become apparent.

Fourth circuit 18 is a debounce circuit with a built in time delay. Mode select switch 20 allows the user to select signal or rezero modes. Inverters $U_2$ and $U_3$ are Schmitt triggers. Resistor $R_6$ and capacitor $C_4$ prevent unwanted momentary switch closures or openings from being passed to circuits 14 and 16. When switch 20 is open and circuit 10 is in signal mode, resistor $R_5$ pulls input 30 of inverter $U_2$ to ground. Output 32 of inverter $U_2$ thus goes into a high state which causes input 34 of inverter $U_3$ to go into a high state after a time delay caused by the combination of resistor $R_6$ and capacitor $C_4$. The high state of input 34 of inverter $U_3$ causes output 28 of inverter $U_3$ to be in a low state. Output 28 of circuit 18 is connected to input 36 of circuit 14 and input 38 of circuit 16.

When switch 20 is closed and circuit 10 is put into the rezero mode, input 30 of inverter $U_2$ is held high by resistor $R_4$ due to the fact that $R_5$ is chosen to be much larger than $R_4$. $R_4$ merely provides electro-static discharge protection. It could be removed with no effect on the functionality of the circuit. Output 32 of inverter $U_2$ is thus low. Input 34 of inverter $U_3$ goes low after a time delay caused by resistor $R_6$ and capacitor $C_4$. Output 28 of circuit 18 is therefore high, switching on switch 22 of circuit 14.

When circuit 10 is in the signal mode, analog switches 22 and 24 are open. Circuit 14 is thus made up of first circuit 14a comprising resistors $R_1$ and $R_2$ (first resistance) and capacitors $C_1$, $C_2$ (first capacitance) and amplifier $U_1$. Damping capacitor $C_3$ (second capacitance) and resistor $R_3$ have no effect on the operation of circuit 14. Second circuit 14b comprises, in addition to $R_1$, $R_2$, $C_1$ and $C_2$ and amplifier $U_1$, damping capacitor $C_3$ and resistor $R_3$. Signal $V_{in}$ passes through circuit 14 to output 26 and appears as a low pass filtered signal $V_{out}$ at output terminal 26. Thus, when switch 20 is open, circuit 14 acts as a two pole active RC filter (first circuit 14a). Resistors $R_1$ and $R_2$ and capacitors $C_1$ and $C_2$ are chosen so that circuit 14 has a Butterworth response with a 3 dB point preferably at 150 Hz. However, a pole in a range from 3 Hz to 20,000 Hz is within the scope of the invention. This configuration provides a low pass noise filter. Persons of ordinary skill in the art will recognize that this circuit 10 could be provided by a variety of filter circuits depending upon the degree of noise attenuation which is required. Thus in a second, less preferred embodiment, components $C_1$ and $C_2$ of first circuit 14a can be omitted and second circuit 14b can be connected directly to input 12.

When switch 20 is closed, circuit 18 causes output 28 to go high as described above. Circuit 10 is thus in the rezero mode. Consider circuit 14, ignoring for the moment circuit 16. When output 28 of circuit 18 goes high due to the closing of switch 20, switch 22 closes. Circuit 14 now becomes second circuit 14b including capacitor $C_3$ in parallel with capacitor $C_2$. $C_3$ is chosen to be large in comparison with $C_2$. Since $C_2$ and $C_3$ are in parallel, and since $C_3$ is much larger than $C_2$, the combination of $R_1$ and $R_2$ with $C_3$ form a dominant pole. Thus circuit 14 is now a low pass filter with a lower corner frequency which filters out the dynamic, pulsatile component of $V_{in}$ and passes only the mean pressure signal. The 3 dB point of this filter is chosen to be at approximately less than 1 Hz preferably in a range from 0.01 Hz to 1 Hz.

Now consider the operation of third circuit 16. Since $C_3$ is large, it takes a long time to charge. Therefore, in the absence of circuit 16, output 26 will have an unacceptably long time to approach final value to sufficient accuracy, in the region of 20 seconds. When line 28 goes high, input 38 of circuit 16 is high. This causes switch 24 to be closed. Resistor $R_3$ is chosen to be much smaller than $R_1+R_2$ (about 100 times). Capacitor $C_3$ therefore charges through resistor $R_3$ rather than through resistors $R_1$ and $R_2$. This causes capacitor $C_3$ to charge very quickly. The rapid charging allows output 26 to approach final value much faster, in the region of 1 second. If input 38 of circuit 16 remains high, input 40 of switch 24 is pulled to ground after a short time delay caused by the combination of resistor $R_7$ and capacitor $C_5$. As a result switch 24 opens after the time delay. Switch 22 remains closed as long as switch 20 remains closed. Capacitor $C_3$ remains connected to resistor $R_2$ and circuit 14 functions as a low pass filter as described above.

Those of ordinary skill in the art will recognize that a leakage current will flow through capacitors $C_2$ and $C_3$ and resistors $R_1$ and $R_2$. This leakage current may cause errors in output 26 ($V_{out}$). Changes in the leakage currents of switches 22 and 24 may also cause errors in $V_{out}$. The selection of switches 22 and 24 and capacitor $C_3$ and their configuration with the other elements of circuits 14 and 16 are important. It has been found that selecting 74HC4316 switches for switches 22 and 24 and a polypropylene capacitor for capacitor $C_3$ minimizes the effects of leakage currents. Switch 20 can be remotely operated at monitor 8 or at rezero device 4.

Persons of ordinary skill in the art will appreciate that the above described invention could be implemented in a variety of ways. For example by means of digital filtering or switched capacitor techniques.

The above description is of a preferred embodiment of the invention. It is intended to be exemplary and not limiting.

We claim:

1. An in vivo pressure signal processing system comprising:

an in vivo pressure transducer for sensing an in vivo pressure and generating a sensor output signal that includes noise, a mean pressure signal, and a dynamic pressure signal;

a first filter circuit having an input connected to said transducer for receiving the sensor output signal, where the first filter circuit filters noise from the sensor output signal and generates a first filter output signal composed of the mean pressure signal and the dynamic pressure signal;

a second filter circuit having an input for receiving the first filter output signal, where the second filter circuit filters the dynamic pressure signal from the first filter output signal and generates a second filter output signal composed of the mean pressure signal;

a first switch for selectively connecting the second filter circuit input to the first filter circuit;

wherein the in vivo pressure may be determined from the first filter output signal when the second filter circuit input is not connected to the first filter circuit and the in vivo pressure transducer may be rezeroed using the second filter output signal when the second filter circuit input is connected to the first filter circuit.

2. The apparatus of 1 wherein the first filter circuit has a low pass characteristic.

3. The apparatus of claim 1 wherein the first filter circuit has a Butterworth response.

4. The apparatus of claim 1 wherein the first filter circuit has a first pole at a first frequency and such that when the first filter circuit and the second filter circuit are electrically connected, the first pole is shifted in frequency such that it dominates the frequency response of the apparatus.

5. The apparatus of claim 4 wherein the first pole is at a higher frequency than the second pole.

6. The apparatus of claim 5 wherein when the first filter circuit is not connected to the second filter circuit, the first pole is in a range from 3 Hz to 20,000 Hz and when the first filter circuit is connected to the second filter circuit, the first pole is in a range from 0.01 Hz to 1 Hz.

7. The apparatus of claim 1 wherein the first filter circuit comprises a first resistance ($R_1$ and $R_2$) and a first capacitance ($C_1$ and $C_2$) and the second filter circuit comprises a second capacitance ($C_3$), the second capacitance being larger than the first capacitance.

8. The apparatus of claim 7 further comprising a third circuit comprising:

a second resistance ($R_3$); and a second switch for selectively electrically connecting the second resistance to the second capacitance.

9. The apparatus of claim 8 wherein the third circuit is connected between the input to the first filter circuit and the second filter circuit for controlling the second switch such that the second switch electrically connects the second resistance to the second capacitance only for a predetermined time.

10. The apparatus of claim 8 wherein the first switch is located remote from the in vivo pressure transducer.

11. The apparatus of claim 8 wherein the first switch is located at the monitor.

12. The apparatus of claim 1, further comprising a monitor connected to receive the first filter output signal.

13. A method for processing an output signal from an in vivo pressure transducer, the output signal comprising noise, a mean pressure signal, and a dynamic pressure signal, the method comprising the steps of:

receiving as an input the output signal from the pressure transducer;

filtering out the noise from the received input in a first filter circuit and outputting a first filter output signal for use in determining in vivo pressure;

temporarily connecting a second filter circuit to the first filter circuit to filter out the dynamic pressure signal while outputting a second filter output signal composed of the mean pressure signal for use in rezeroing the pressure transducer.

14. The method of claim 13 wherein the step of filtering out the noise includes the step of passing the received input through a low pass filter.

15. The method of claim 13 wherein the step of filtering out the noise includes the step of passing the received input through a filter having a Butterworth response.

16. The method of claim 13 wherein the first filter circuit has a first pole at a first frequency and such that the step of temporarily connecting the second filter circuit to the first filter circuit shifts the first pole in frequency such that it dominates the frequency response of the apparatus.

17. The method of claim 16, wherein the step of temporarily connecting the second filter circuit to the first filter circuit shifts the first pole of the first filter circuit from the range 3 hz–20000 hz to the range 0.1 hz–1.0 hz.

* * * * *